United States Patent [19]
Woiszwillo

[11] Patent Number: 5,525,519
[45] Date of Patent: Jun. 11, 1996

[54] METHOD FOR ISOLATING BIOMOLECULES FROM A BIOLOGICAL SAMPLE WITH LINEAR POLYMERS

[75] Inventor: James E. Woiszwillo, Milford, Mass.; Fred Rothstein, Long Beach Calif.

[73] Assignee: Middlesex Sciences, Inc., Milford, Mass.

[21] Appl. No.: 817,610

[22] Filed: Jan. 7, 1992

[51] Int. Cl.$^6$ .................................... G01N 33/487
[52] U.S. Cl. .................. 436/88; 436/17; 436/513; 436/539; 436/503
[58] Field of Search ................... 436/17, 503, 512, 436/815, 539, 540, 88, 513

[56] References Cited

U.S. PATENT DOCUMENTS

| | | | |
|---|---|---|---|
| Re. 31,268 | 6/1983 | Hansen | 260/112 B |
| 3,631,018 | 12/1971 | Shanbroom et al. | 260/112 B |
| 3,652,530 | 3/1972 | Johnson et al. | 260/112 B |
| 3,790,552 | 2/1974 | Johnson et al. | 260/112 B |
| 3,869,436 | 3/1975 | Falksveden | 260/112 B |
| 4,016,039 | 4/1977 | Schreiber | 195/66 R |
| 4,093,606 | 6/1978 | Coval | 260/112 B |
| 4,115,375 | 9/1978 | Pederson | 260/112 R |
| 4,124,576 | 11/1978 | Coval | 260/112 B |
| 4,164,495 | 8/1979 | Hansen | 260/112 B |
| 4,165,370 | 8/1979 | Coval | 424/85 |
| 4,543,210 | 9/1985 | Mitra et al. | 260/112 |
| 4,578,218 | 3/1986 | Saundry et al. | 260/112 |
| 4,683,294 | 7/1987 | Van Wijnendaele et al. | 530/371 |
| 4,692,331 | 9/1987 | Uemura et al. | 424/85 |
| 4,740,304 | 4/1988 | Tjerneld et al. | 210/639 |
| 4,822,535 | 4/1989 | Ekman et al. | 264/4.3 |
| 4,874,708 | 10/1989 | Makula et al. | 435/272 |
| 4,910,182 | 3/1990 | Hums et al. | 502/402 |
| 5,135,875 | 8/1992 | Meucci et al. | 436/17 X |
| 5,177,194 | 1/1993 | Sarno et al. | 530/412 |
| 5,288,853 | 2/1994 | Bhattacharva et al. | 530/383 |

FOREIGN PATENT DOCUMENTS

| | | |
|---|---|---|
| 1064396 | 10/1979 | Canada. |
| 3430320 | 3/1985 | Germany. |
| 1109170 | 8/1984 | U.S.S.R. . |
| W090/03164 | 9/1989 | WIPO . |

OTHER PUBLICATIONS

Spencer et al., "Use of Water-Soluable polymers in the preparation of Blood Group Diagnostic Reagents," Med. Lab. Sciences 42(2), 1985 pp. 115–117.

Farrugia et al., "Studies of the Procurement of Coagulation Factor VIII: Selective Precip. of Factor VIII with Hydrophilic Polymers," Titromb. Hoemostasis, 51 (3), 1984, 338–342.

Hasko et al., "Fractionation of Plasma Proteins with PEG," Haemotologia, vol. 14 (2), 1981, pp. 199–206.

Vinella et al., "Isolation of Soluable Immune Complexes from Human Serum: Combined Use of Polyethlene Glycol Prec., Gel Filtration, and . . . ," Method in Enz. vol. 74, 1981, 644–663.

Weisen et al., "Gel Diffusion reactions and Biological Properties of Paeonia Tannin," Plyto Path. Z, vol. 93 (1), pp. 56–68, 1978.

Shibata et al., "Immunoglobutin with Decreased Complement Activity by Pree. with Polyethlene Glycol and Aminoacetic Acid.", CA 103 (8): 59287X.

Hamma et al., "The Use of Aqueous Tw–Phase Systems to Concentrate and Purify Bovine Leukemia Virus Outer Envelope Protein gp 51," Biot & App. Biochem, Nov. 1989, 296–306.

Albertsson et al., "separation of Membrane Components by Portition in Detergen–Containing Polmer Phase System. . . ", J. of Chrom. 215, 1981, 131–141.

Clamagirand, C., et al., "Partial Purification and Functional Properties of an Endoprotease from Bovine Neurosecretory Granules Cleaving Proocytocin/Neurophysin Peptides at the Basic Amino Acid Doublet," Biochemistry, 26(19):6018–6023 (1987).

Feldman, J. A., et al., "Seminterpenetrating Networks Based on Triazine Thermoset and N–Alsylamide Thermoplastics," Am. Chem. Soc. Symposia Series, 367:244–268 (1988).

Georgiou, M., "Functional and Physical Characteristics of Rat Levdig Cell Populations Isolated by Metrizamide and Percoll Gradient Centrifugation," Biology of Reproduction, 37:335–341 (1987).

Green, A. A., et al., "Protein Fractionation on the Basis of Solubility in Aqueous Solutions of Salts and Organic Solvents," Methods in Enzymology, Ed. C. Kaplan, 1:99–121 (1955).

He. D., et al., "Mast–Cell Heterogeneity; Functional Comparison of Purified Mouse Cutaneous and Peritoneal Mast Cells," The Society for Investigative Dermatology, Inc., 95(2) (1990).

Heuck, C. C., et al., "Rapid Development of Immunoprecipitins in Agarose Gel." Clinica Acta, 98:195–199 (1979).

Ingham, K. C., "Precipitation of Proteins with Polyethylene Glycol," Methods in Enzymology, 182:301–306 (1990).

Polson, et al., "The Fractionation of Protein Mixtures by Linear Polymers of High Molecular Weight," Biochim. Biophys. Acta. 82:463–475 (1964).

Sanbar, et al., "Hypolipidemic Effect of Polyvinvlpyrrolidone in Man," Circulation, 38:771–776 (1968).

Schultze, H. E., et al., "Molecular Biology of Human Proteins–With Special Reference to Plasma Proteins," 1:240–317 (1966).

Sperling, L. H., "Interpenetrating Polymer Networks and Related Materials," Plenum Press, New York (1981).

Strong, M. J., et al., "Isolation of Fetal Mouse Motor Neurons on Discontinuous Percoll Density Gradients," In Vitro Cellular & Developmental Biology, 25(10):939–945 (1989).

van Suylichen, et al., "The Efficacy of Density Gradients for Islet Purification: A Comparison of Seven Density Gradients," Transplant International, 3:156–161 (1990).

Zeppezauer, et al., "Protein precipitation by uncharged water-soluable polymers," Biochim. Biophys. Acta 94:581–583 (1965).

Primary Examiner—Steven Weinstein
Assistant Examiner—Milton I. Cano
Attorney, Agent, or Firm—Jones & Askew

[57] ABSTRACT

A method and composition for isolating biomolecules from a biological sample wherein the sample is mixed with a soluble, linear polymer, such as polyvinylpyrrolidone, to form a precipitate. The biomolecule of interest is found in the precipitate or is isolated from the supernatant.

25 Claims, 1 Drawing Sheet

METHOD FOR ISOLATING BIOMOLECULES FROM A BIOLOGICAL SAMPLE WITH LINEAR POLYMERS

The present method relates to the separation and isolation of biomolecules and more specifically relates to the use of polymers to isolate proteins from biological samples.

BACKGROUND OF THE INVENTION

Protein Isolation

Protein isolation is an important tool in biological research, clinical diagnostics and the production of pharmaceuticals, especially production by recombinant techniques. The scientific researcher must obtain a protein quickly while retaining high specific activity; the clinician must identify proteins in biological samples in order to make an accurate diagnosis; and the molecular biologist must recover and purify large quantities of proteins produced by recombinant organisms.

Scientists have traditionally isolated proteins by precipitating them from biological samples with salts, such as ammonium sulfate, or organic solvents, such as ethanol. Exposure to the chemicals used in such methods often causes protein denaturation. In addition, separation of the proteins from the precipitating chemical is difficult and may cause further denaturation.

The ammonium sulfate precipitation technique, also known as "salting out," is based on the fact that the solubility of most proteins decreases at high electrolyte concentration. Sulfate is used because multivalent ions are more effective than monovalent ions. This procedure is usually carried out in the cold (0°–4° C.) with control of pH close to neutrality. Different classes of proteins precipitate depending on the concentration of salt added. The disadvantage to this method is the difficulty of removing residual salt from the precipitate or supernatant. Often dialysis is used, but is very time consuming.

Organic solvents are often used for fractional precipitation of proteins. However, there is a risk that the solvent will denature the protein unless kept at a temperature near the freezing point. In addition, the solvent must be removed from the protein. A solvent such as ethanol is generally removed by lyophilizing the precipitated proteins.

Recent advances in protein purification have centered around the development of high performance ion exchange, affinity chromatography, hydrophobic interactions and gel filtration chromatography. The biological sample is loaded onto a chromatography column and is eluted with the appropriate solvent into fractions that are analyzed for protein activity. This method is expensive, time consuming, and poorly suited for large scale protein purification.

Many scientist continue to use traditional methods alone or in combination with the recently developed chromatography procedures. For example, after precipitation of a protein from a biological sample with ammonium sulfate, protein is separated from the ammonium sulfate salt by chromatography. Often the protein loses activity or becomes denatured during one or more steps of the procedure, resulting in a low yield or inaccurate identification.

Polymer Studies

In the mid 1960's, Polson et al., *Biochim. Biophys. Acta* 82:463–475 (1964), analyzed a variety of high molecular weight polymers for purifying proteins including polyethylene glycol (PEG), dextran, nonylphenol-ethoxylates (NPEs), polyvinyl alcohol (PVA) and polyvinylpyrrolidone (PVP). Polson et al. concluded that PEG is the most suitable of the tested polymers for protein precipitation. The disadvantage to PEG is that it must be removed from the protein either by passage through a DEAE or cellulose column under conditions that adsorb the proteins and wash out the PEG with the effluent or by adding ethanol to precipitate the proteins from the supernatant, leaving the PEG in the supernatant. Polson et al. explicitly caution against the use of PVE, PVP and NPEs because of their high intrinsic viscosities and because, according to their observations, the polymers cause significant protein denaturation. The results of Polson et al. were confirmed and extended by Zeppezauer and Brishammar, *Biochim. Biophys. Acta* 94:581–583 (1965) who precipitated kidney proteins with three high molecular weight preparations of Polyox™ a PEG resin obtained from Union Carbide Corp. (Danbury, Conn.).

Polyethylene glycol (PEG), also known as poly(oxyethylene)glycol, is a condensation polymer of ethylene oxide and water having the general chemical formula $HO(CH_2CH_2O)_nH$. PEG is used as a water-soluble lubricant for rubber, textile and metal manufacture; in food, cosmetics, water paints, paper coatings, and polishes; and as an ointment base in pharmaceuticals.

Dextran is a term applied to polysaccharides produced by bacteria growing on a sucrose substrate. Native dextrans produced by bacteria such as *Leuconostoc mesenteroides* and *Lactobacteria dextranicum* usually have a high molecular weight. The lower molecular weight dextrans used as plasma volume expanders or blood flow adjuvants are usually prepared by depolymerization of native dextrans or by synthesis.

NPEs are a class of long chained compounds often used as surfactants. They are usually derivatized to meet the desired solubility requirements.

PVA is a polymer prepared from polyvinyl acetates by replacement of the acetate groups with hydroxyl groups and has the formula $(CH_2CHOH)_n$. Most polyvinyl alcohols are soluble in water and are used as elastomers in the plastics industry, as viscosity increasing agents in the pharmaceutical industry, and as ophthalmic lubricants.

PVP is a non-ionogenic, hydrophilic polymer having a mean molecular weight ranging from approximately 10,000 to 700,000 and the chemical formula $(C_6H_9NO)_n$. PVP is also known as poly[1-(2-oxo-1-pyrrolidinyl)ethylene], Povidone™, Polyvidone™, RP 143™, Kollidon™, Peregal ST™, Periston™, Plasdone™, Plasmosan™, Protagent™, Subtosan™, and Vinisil™. PVP is non-toxic, highly hygroscopic and readily dissolves in water or organic solvents. PVP has a wide variety of uses such as in pharmaceuticals, as a complexing agent, and for the detoxification of chemicals. It is also used in tableting, photographic emulsions, cosmetics, detergents, adhesives, and beer and wine clarification. PVP was used as a blood plasma expander during World War II, but when high molecular weights were found to be adsorbed in tissues this use was abandoned. intravenous PVP has been used to decrease human serum lipids as described by Sanbar and Smet, *Circulation* 38:771–776 (1968).

PEG, dextran, PVA and PVP are commercially available from chemical suppliers such as the Sigma Chemical Company (St. Louis, Mo.). NPEs require custom synthesis and can be ordered from special chemical producers.

Recombinant Techniques

Many proteins, such as for example, human growth hormone and insulin, are now produced by recombinant techniques. The gene encoding the protein is inserted into a bacterial or viral vector causing production of large quantities of the protein which must then be isolated from the other proteins in the growth media, or fermentation fluid. A rapid, inexpensive method for the purification of proteins produced by recombinant techniques would help reduce the costs and improve the recovery of proteins produced in this manner.

Drug Disposition

A sufficient amount of pharmaceutical agent or drug must reach its site of action in order to exert a desired effect. Drug absorbed into the blood from the site of administration often binds to proteins, such as albumin, that retard the delivery of drug to the site of action. A drug having a higher affinity for serum proteins will require a larger dose to achieve the desired effect.

During pharmaceutical development, drug disposition studies are performed to determine the amount of drug bound to serum protein. After administration of drug, serum proteins are isolated by chromatography or are precipitated by chemicals such as ammonium sulfate. The concentration of the drug in the protein fraction is determined and is compared with the total concentration of drug found in the intact sample through analytical techniques. These methods are time consuming and do not provide sufficient information concerning the identity of the proteins to which the drug is bound.

Urine samples are also analyzed for drug or drug metabolite concentration to ensure that the drug is excreted and is not retained by the body. Interfering proteins are often separated from drug as described above using time consuming procedures.

Albumin Isolation

Albumin is a simple protein distributed throughout the tissues and fluids of plants and animals, well known for its presence in the white portion of poultry eggs. Albumin is soluble in water and is easily denatured by heat, acid or neutral solutions. Bovine serum albumin (BSA) is derived from bovine blood and is often used in in vitro biological studies. Normal human serum albumin is obtained by fractionating blood plasma proteins from healthy persons and is used as a transfusion material. Serum albumin is also used in diagnostics such as, for example, the use of radioiodinated serum albumin in determining blood volume and cardiac output. Therefore, there is a great need for an inexpensive method of producing large quantities of purified albumin.

Immunoglobulin Isolation

The immunoglobulins IgG, IgM, IgA, IgE and IgD, which are found in the gamma globulin fraction of vertebrate serum proteins, constitute the circulating antibody population and provide the humoral immune response necessary to fight infection and disease. A measurement of the serum globulin to albumin ratio provides a good indication of the presence of an immune response to infection and an individual's ability to combat the infection. An abnormally high concentration of globulin in the serum is often an indication of a hyperproliferative disorder such as myeloma or Bence Jones proteins. Purified immunoglobulins are necessary for scientific research, especially in the development of vaccines, and for passive immunization of individuals who have been recently exposed to a bacteria or virus for which a vaccine is not yet available. Therefore, a rapid method for isolating immunoglobulins from blood for research, diagnostic or therapeutic purposes is necessary.

Antibodies

Monoclonal antibodies are created by fusing a normal antibody-producing lymphocyte from the spleen of a recently immunized experimental animal to a myeloma cell line to form a hybridoma. The myeloma cell causes the continuous production of the antibody of interest which is usually recovered from ascites fluid. Monoclonal antibodies must be isolated from the other proteins present in the ascites fluid before use as reagents in diagnostic kits, scientific research, or coupled to a drug to provide a "magic bullet" that is directed to a target site such as a malignant tumor. Polyclonal antibodies are produced by injecting an animal, such as a mouse, rat or rabbit, with an antigen, collecting blood, and isolating the immunoglobulin fraction that binds to the antigen, usually by passage of the immunoglobulin fraction through an affinity column to which antigen has been immobilized. The resulting polyclonal antibodies are used for the same purposes as monoclonal antibodies described above except that the specificity of a polyclonal antibody for a particular antigen is not as great. An inexpensive, rapid method of isolating and purifying monoclonal or polyclonal antibodies would greatly simplify antibody production.

Spinal Fluid and Urine Analysis

Medical diagnosis of disease or disorders is often achieved by analyzing bodily fluids such as spinal fluid or urine. Separation of biomolecules from interfering substances in the spinal fluid or urine sample would provide a faster, more reliable diagnosis.

What is needed is a biomolecule isolation method that is simple, inexpensive and fast, yet allows for the isolation of a relatively pure, active biomolecule.

It is therefore an object of the present invention to provide a non-denaturing method of isolating a biomolecule.

It is a further object of the present invention to provide a rapid, reproducible method of isolating a relatively pure protein.

It is a further object of the present invention to provide a method of isolating a biomolecule from a biological sample in a single step.

It is a further object of the present invention to provide a method of isolating large quantities of relatively pure protein.

It is a further object of the present invention to provide a method of determining the globulin to albumin ratio in serum.

It is a further object of the present invention to provide a method of determining the disposition of a drug in serum proteins.

SUMMARY OF THE INVENTION

A method and composition for the isolation of an active biomolecule, such as a protein, from a biological sample are provided. A soluble, linear polymer is added to the sample to form a precipitate. The biomolecule of interest is isolated from either the precipitate or the supernatant. Biomolecules of interest are isolated from the supernatant by subsequent polymer precipitation or precipitation with a zinc compound.

Isolation of any particular biomolecule depends on the pH of the sample before, during or after addition of the polymer. The sample is adjusted to a predetermined pH before or after polymer addition with an acid or base, preferably an amino acid or a mixture of amino acids. Alternatively, the pH of the linear polymer is adjusted and the pH-adjusted polymer is added to the sample to cause precipitation and selective biomolecule isolation in a single step. The preferred concentration of amino acids used for the pH adjustment is dependent on the pH desired for the isolation procedure.

Preferably, the polymer is an aqueous solution of polyvinylpyrrolidone. Alternatively, the polymer is a mixture of polyvinylpyrrolidone and one or more additional soluble, linear polymers, such as polyethylene glycol, dextran, nonylphenol ethoxylates or polyvinyl alcohol, most preferably a mixture of polyvinylpyrrolidone and polyethylene glycol.

In the preferred method, immunoglobulins are isolated from blood serum by first adjusting the pH of a polymer solution of polyvinylpyrrolidone and polyethylene glycol to a neutral pH. The pH is adjusted with an amino acid solution containing glutamic acid, histidine, and lysine. The polymer solution is then added to the sample to precipitate a relatively pure immunoglobulin fraction, leaving interfering proteins, such as albumin, and other substances in the supernatant.

A method for the disposition of a drug in serum proteins is also described by isolating the globulin fraction, precipitating albumin from the supernatant, and then measuring the amount of a drug in each fraction.

A method is also provided for determining the globulin to albumin ratio in serum samples for diagnostic purposes by isolating the globulin and albumin as described above and then determining the concentration of each and their ratio in the sample.

DETAILED DESCRIPTION OF THE INVENTION

Figure 1:
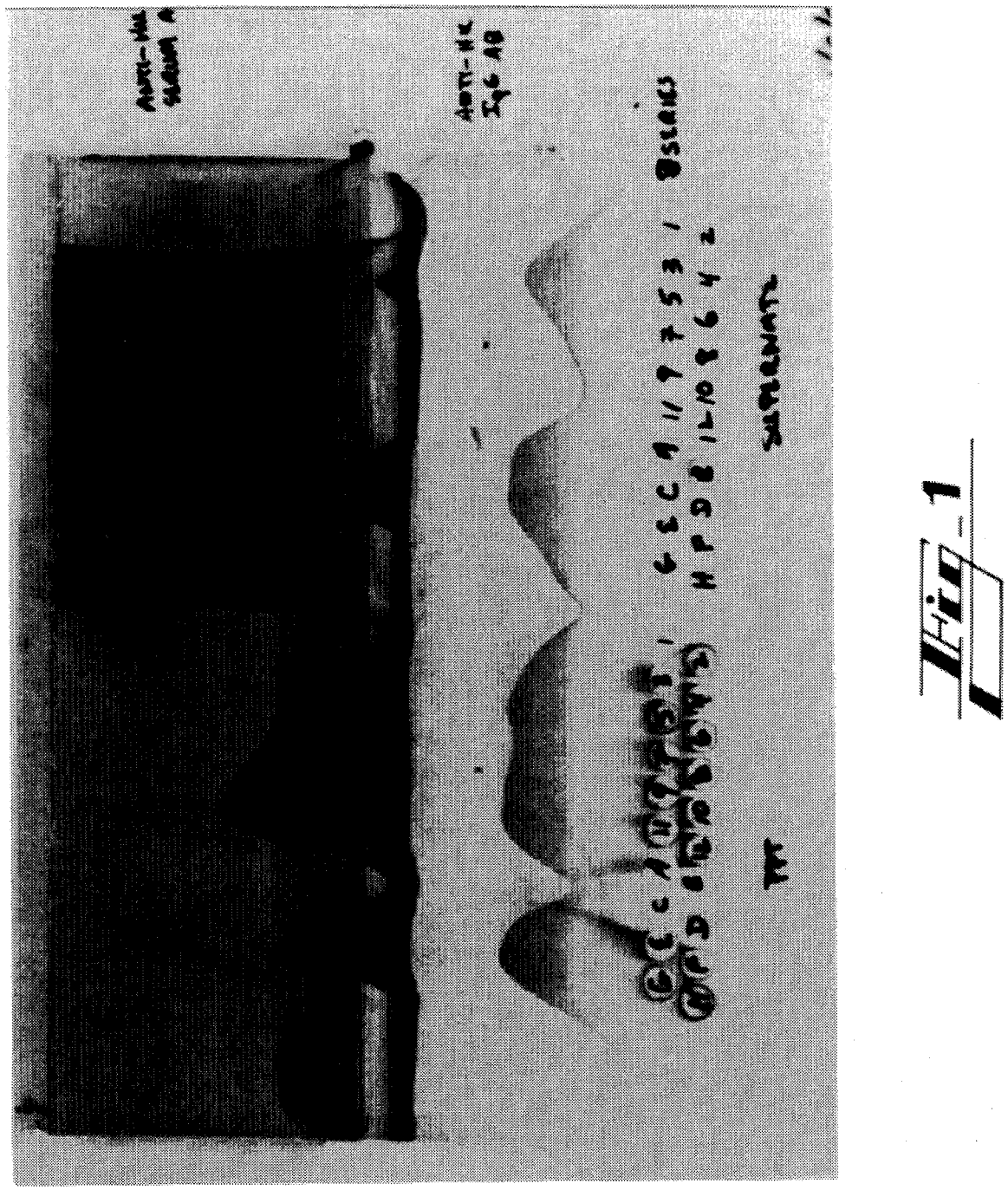
FIG. 1 is a drawing of an electrophoretic gel showing separation of globulin and albumin with a polymer mixture of PEG and PVP.

A method and composition are provided for the isolation of a biologically active biomolecule from a biological sample with linear polymers. Biomolecules to be isolated include proteins, lipids, nucleic acids, carbohydrates, and non-protein hormones.

The biomolecule of interest is isolated by adding a sufficient amount of a soluble, linear polymer, or mixture of polymers, to the biological sample to form a precipitate. The biomolecule is then isolated from either the precipitate or supernatant by decantation or subsequent precipitation.

Selection of a particular biomolecule of interest from other biomolecules and interfering substances in the sample is achieved by adjusting the pH of the sample to a predetermined value either before, after, or during addition of the polymer. Preferably, the sample is adjusted to a predetermined pH between 4 and 9.2 by adding a pH-adjusted polymer solution to the sample to allow pH adjustment, precipitation and isolation of the desired biomolecule in a single step. The pH of the polymer solution is adjusted by the addition of an acid or base, preferably an amino acid or amino acid mixture that results in minimal salt formation. Alternatively, the sample is adjusted, either before or after addition of the polymer, by adding the acid, base, or amino acid solution directly to the sample.

Isolation of a biomolecule of interest from the resulting supernatant is achieved by adding a second polymer solution having a different mixture of polymers or a different pH, or by adding a zinc compound such as zinc sulfate to precipitate the biomolecule of interest from the supernatant.

Polymers Used to Precipitate Biomolecules

The biomolecule is isolated by adding a sufficient amount of a water soluble, linear polymer such as polyethylene glycol (PEG), dextran, nonylphenol-ethoxylates (NPEs), polyvinyl alcohol (PVE), polyvinylpyrrolidone (PVP), or a mixture thereof, to form a precipitate. Preferably, the polymer is an aqueous solution of PVP having a molecular weight between 10,000 and 360,000, most preferably 40,000. PVP is dissolved in water in a concentration between 1 and 30 g/100 ml depending on the molecular weight of the polymer. Most preferably 20 g/100 ml of a 40,000 molecular weight (MW) solution of PVP is used. The volume of polymer added to the sample varies depending on whether the biomolecule of interest is to be retained in the supernatant or precipitated.

Polymer Networks

The soluble, linear polymer is added as a sole polymer, as a mixture of two or more polymers, or in a polymer network. A polymer network is a non-covalent linkage of polymers in a homogenous, insoluble, cross-linked or honeycomb-like structure that does not interfere with the water-binding properties of the linked polymers. Polymer networks are described in detail by Sperling, L. H. in the book entitled "Interpenetrating Polymer Networks and Related Networks" Plenum Press, N.Y., 1981, the teachings of which are incorporated herein. An aromatic dicyanine compound, such as 4,4-bisphenol A dicyanate, or a mixture of dicyanate and cyanate compounds, as described by Feldman and Huang in *Am. Chem. Soc. Symposia* Series, 367:244–268 (1988) which is incorporated by reference herein, provide suitable reagents for networking the polymers.

Preferably, two volumes of a dicyanate compound is combined with one volume of a polymer or polymer mixture to create the network. When the mixture is heated above the melting temperature of the dicyanate, the dicyanate esters undergo a cyclotrimerization reaction forming triazine rings and a relatively open network which immobilizes the polymer molecules. Preferably, the mixture is heated to a temperature between 80° C. and 90° C. for approximately 40 minutes. The resulting cross-linked structure remains thermally and mechanically stable and provides a homogenous mixture of water-absorbing polymers.

The network of polymers is preferably added to a sample as a sponge or honeycomb-like structure to rapidly isolate the biomolecule of interest. The polymers dispersed in the network absorb water in the sample, causing precipitation. The polymer network is then removed from the sample. The biomolecule of interest is isolated from the precipitate or eluted from the polymer network with a suitable solvent, such as water.

Adjustment of pH

The pH of the polymer or sample is preferably adjusted to a predetermined pH between 4 and 9.2 with an acid or base solution having a pH between 2 and 10.5. The acid or base solution is added to the polymer solution that is subsequently added to the sample, or the acid or base solution is added directly to the sample either before or after addition of the polymer.

Preferably, the acid or base solution contains a small molecular weight hapten possessing a charged carboxyl group or charged amino acid group. For example, the acid or base solution can contain amino acids or a small molecular weight silane basic silane compound that will preferably avoid the formation of salts.

Most preferably, the pH is adjusted with a solution containing a charged amino acid, such as aspartic acid, glutamic acid, lysine, arginine, histidine or salts thereof; an uncharged polar amino acid such as glycine, serine, threonine, cysteine, tyrosine, asparagine, or glutamine or salts thereof; or a mixture of charged and uncharged polar amino acids such as a mixture of glycine, cysteine, and lysine, or salts thereof, to achieve the desired pH.

The optimal pH is determined by establishing a sample pH gradient with the appropriate acid or base mixture by adding various pH-adjusted polymers to the sample or adding polymer to aliquots of the sample adjusted to various pHs, and analyzing the resulting supernatant or precipitate by conventional means such as gel electrophoresis, immunoblot, or enzyme-linked immunosorbant assay (ELISA) to determine which pH provides the greatest amount of the biomolecule of interest at the highest level of purity.

Ratio of Polymer to Sample

A sufficient amount of the polymer is added to a biological sample to either precipitate the biomolecule of interest or precipitate interfering biomolecule and other substances, leaving the biomolecule of interest in the supernatant. A polymer to sample volume ratio of from 1:1 to 20:1 will provide optimal separation. Preferably, the ratio of polymer to sample volume is 8:1.

The amount of polymer needed depends on the amount of water present in the sample. Samples containing larger quantities of water, such as urine, will require more polymer than more concentrated samples, such as blood serum.

Isolation of Proteins

It is believed that the combination of PVP and PEG successfully separate proteins by absorbing water from the sample by two different mechanisms. PVP binds water through its peptide bonds while PEG binds water through its hydroxyl groups. It is believed that these combined absorption mechanisms create a pure separation of proteins unknown in currently available protein purification and isolation methods.

Isolation of Immunoglobulins

For example, the method described herein is applied to the isolation of one or more proteins as follows: An immunoglobulin is isolated from a human blood serum sample with an aqueous polymer mixture of PVP and PEG, the PEG having a molecular weight range between 200 and 35,000. PVP having a molecular weight of 40,000 and PEG having a molecular weight of 3500 is preferred. Preferably, the PEG is dissolved in water and PVP is added to the aqueous PEG solution. The concentration of each polymer is preferably between 1 and 30 g/100 ml, most preferably 20 g/100 ml or 20%, for PEG having a molecular weight of 3500. Equal concentrations of PVP and PEG will provide the most favorable isolation of protein.

The polymer solution is adjusted to a neutral pH between 6.8 and 7.2 with an acid or base solution prior to addition of the polymer solution to the sample. Preferably, the pH of the approximately 1.2 mg/ml glutamic acid, approximately 1.5 mg/ml histidine, and approximately 1.5 mg/ml lysine.

Approximately 8 volumes of the pH-adjusted PVP/PEG polymer mixture is added to one volume of blood serum to form a precipitate. Most preferably, 4 ml of polymer is added to 0.5 ml of serum. The supernatant retains the albumin fraction while the precipitate contains the immunoglobulin fraction.

Albumin is precipitated from the supernatant by the addition of a sufficient amount of a zinc compound, most preferably zinc sulfate heptahydrate.

Immunoassay

It will be understood by those skilled in the art that the biomolecule isolation method described above can be used in an immunoassay for detection of specific antibodies in a biological sample. Antigen is mixed with a biological sample containing antibodies specific for the antigen, and the mixture is incubated for a sufficient amount of time to create antibody-antigen conjugates. Isolation of the antibody-antigen conjugates from free antigen is achieved in a manner similar to the above-described immunoglobulin isolation method.

Biological Fluids

It will be understood by those skilled in the art that the methods provided herein are useful in isolating biomolecules from biological fluids other than blood serum including blood plasma, urine, spinal fluid, fermentation fluid, lymph fluid, tissue culture fluid and ascites fluid.

The protein isolation methods described above will be further understood with reference to the following non-limiting example.

EXAMPLE

Effect of pH on Isolation of Immunoglobulins from Human Serum with a Polymer Mixture of PVP and PEG Immunoglobulins were isolated from human AB serum with a polymer mixture of PVP (MW=4000) and PEG (MW=3500). A 20% solution of each polymer, obtained from Sigma, St. Louis, Mo., was prepared by adding 20 grams of polymer to 100 ml of either 10× phosphate buffered saline (PBS), 1× PBS, or distilled water.

The pH of each 20% polymer solution was adjusted to a pH of approximately 7 with an amino acid solution containing 1.1 g/ml glycine hydrochloride, 1.21 g/ml cysteine and 1,46 g/ml lysine in water. Each amino acid was obtained from Sigma (St. Louis, Mo.). The final concentration of amino acids in the polymer solution was 10 mM.

Ten milliliters of the pH-adjusted polymer solution was added to 1.25 ml of human AB serum. The volume of aqueous PVP or PEG added to each sample is set forth below in Table I.

TABLE I

| | Amount of PVP and PEG added to Protein Samples | |
|---|---|---|
| Sample | 20% PVP in Water | 20% PEG in Water |
| 1 | 5 ml | 5 ml |
| 2 | 10 ml | 0 ml |
| 3 | 9 ml | 1 ml |
| 4 | 8 ml | 2 ml |
| 5 | 7 ml | 3 ml |
| 6 | 6 ml | 4 ml |
| 7 | 5 ml | 5 ml |
| 8 | 4 ml | 6 ml |
| 9 | 3 ml | 7 ml |
| 10 | 2 ml | 8 ml |
| 11 | 1 ml | 9 ml |
| 12 | 0 ml | 10 ml |

The volume of polymer dissolved in either 10× PBS, 1× PBS, or water is set forth below in Table II.

TABLE II

| | Volume of Polymer Dissolved in Solution | | |
|---|---|---|---|
| Sample | Polymer in 10X PBS | Polymer in 1X PBS | Polymer in H$_2$O |
| A | 10.0 ml | 0.0 ml | 0.0 ml |
| B | 5.0 ml | 5.0 ml | 0.0 ml |
| C | 2.5 ml | 7.5 ml | 0.0 ml |
| D | 1.0 ml | 9.0 ml | 0.0 ml |
| E | 0.0 ml | 5.0 ml | 5.0 ml |
| F | 0.0 ml | 2.5 ml | 7.5 ml |
| G | 0.0 ml | 1.0 ml | 9.0 ml |
| H | 0.0 ml | 0.0 ml | 10.0 ml |

Both sets of samples were incubated at 4° C. for 18 hours. A precipitate formed. The supernatant was removed from the precipitate by decantation. The precipitate was redissolved in phosphate buffered saline. Both the precipitate and the supernatant for each sample were run on a two-dimensional agarose electrophoretic gel for 18 hours. The results are shown in FIG. 1.

A 8 µl aliquot of the redissolved precipitate from each sample was loaded into wells and migrated on the left portion of the gel. A 8 µl aliquot of the supernatant from each sample was loaded into wells and migrated on the right portion of the gel. Serum proteins were detected by precipitation with a whole molecule anti-human serum antibody (Sigma, St. Louis, Mo.) as shown in the upper frame of FIG. 1. Immunoglobulins were detected by precipitation with an anti-human whole IgG antibody (Sigma, St. Louis, Mo.) as shown in the lower frame of FIG. 1. Precipitates were stained with the protein assay reagent Coomassie Blue. (Pierce Chemical Co., Rockford, Ill.)

As shown in FIG. 1, the amount of globulin in the precipitate is maximized in samples 9–12, G and H. These samples also have virtually no globulin in the supernatant.

Modifications and variations of the present biomolecule isolation method will be obvious to those skilled in the art from the foregoing detailed description of the invention. Such modifications and variations are intended to come within the scope of the appended claims.

I claim:

1. A method of isolating at least one biomolecule from a biological sample comprising the steps of:
   a) adding a sufficient amount of a solution of at least two soluble, linear polymers to a biological sample solution to form a precipitate, wherein a first polymer is polyvinylpyrrolidone and a second polymer is polyethylene glycol, and adjusting the solution to a predetermined pH; and
   b) separating the precipitate from the supernatant; thereby isolating a biomolecule from the biological sample in either the supernatant or precipitate.

2. The method of claim 1 wherein the pH of the solution is adjusted to a predetermined pH by adjusting the pH of the polymers with an amino acid before addition to the solution.

3. The method of claim 1 wherein the pH of the solution is adjusted with an amino acid before or after addition of the polymers.

4. The method of claim 1 wherein the polymers are added as an insoluble network of non-covalently linked polymer molecules.

5. The method of claim 1 wherein the ratio of polymers to biological sample solution is approximately 8:1.

6. The method of claim 1 wherein the polyvinylpyrrolidone has a molecular weight of approximately 40,000.

7. The method of claim 1 wherein the first polymer is a 20% aqueous solution of polyvinylpyrrolidone.

8. The method of claim 1 wherein the polyvinylpyrrolidone is first mixed with the polyethylene glycol and the polymer mixture is added to the sample.

9. The method of claim 8 wherein the ratio of polyvinylpyrrolidone to polyethylene glycol in the polymer mixture is 1:1.

10. The method of claim 1 wherein the polyvinylpyrrolidone has a molecular weight of approximately 40,000 and the polyethylene glycol has a molecular weight of approximately 3500.

11. The method of claim 1 wherein the adjusted pH of the solution is between 4.0 and 9.2.

12. The method of claim 1 wherein the biomolecule is selected from the group consisting of proteins, carbohydrates, non-protein hormones, and nucleic acids.

13. The method of claim 12 wherein the protein is an immunoglobulin.

14. The method of claim 1 wherein the biological sample solution is selected from the group consisting of blood serum, blood plasma, urine, and spinal fluid, fermentation fluid, lymph fluid, tissue culture fluid, and ascites fluid.

15. The method of claim 1 wherein the polyethylene glycol has a molecular weight of approximately 3500.

16. An assay for determining the albumin to globulin ratio in plasma comprising the steps of:
   a) adding a sufficient amount of a polymer solution of polyvinylpyrrolidone and polyethylene glycol to the plasma to precipitate the globulin, leaving the albumin in the supernatant, wherein the pH of the plasma is adjusted to an approximately neutral pH;
   b) separating the precipitate from the supernatant;
   c) measuring the concentrations of globulin and albumin; and
   d) calculating the ratio of albumin to globulin.

17. The assay of claim 16 wherein the pH of the plasma is adjusted by adjusting the pH of the polymer solution to a predetermined value before addition to the plasma.

18. A method for determining the disposition of a drug in serum proteins comprising the steps of:
   a) adding a sufficient amount of an aqueous solution of polyvinylpyrrolidone and polyethylene glycol to serum to precipitate the globulin, wherein the pH of the serum is adjusted to a predetermined value;
   b) separating the precipitate from the supernatant, thereby isolating globulin-bound drug and albumin-bound drug in either the precipitate or supernatant; and
   c) analyzing the precipitate and supernatant to detect the drug.

19. A method of isolating at least one protein from a biological sample solution comprising the steps of:
   a) combining polyvinylpyrrolidone with polyethylene glycol to form a polymer mixture;
   b) adjusting the pH of the polyvinylpyrrolidone and polyethylene glycol mixture to a predetermined value with an acid or base;
   c) adding a sufficient amount of the pH-adjusted polyvinylpyrrolidone and polyethylene glycol mixture to the sample solution to form a precipitate; and
   d) separating the precipitate from the supernatant, thereby isolating a protein from the biological sample in either the supernatant or precipitate.

20. The method of claim 19 wherein the polyvinylpyrrolidone has a molecular weight of approximately 40,000.

21. The method of claim 19 wherein the biological sample solution is selected from the group consisting of blood serum, blood plasma, urine, and spinal fluid, fermentation fluid, lymph fluid, tissue culture fluid, and ascites fluid.

22. The method of claim 19 wherein the molecular weight of polyvinylpyrrolidone is approximately 40,000 and the molecular weight of polyethylene glycol is approximately 3500.

23. The method of claim 19 wherein the ratio of polyvinylpyrrolidone to polyethylene glycol is 1:1.

24. The method of claim 19 wherein the mixture is an insoluble network of non-covalently linked polymer molecules.

25. The method of claim 19 wherein the concentration of polyvinylpyrrolidone and polyethylene glycol is approximately 20%.

* * * * *